(12) United States Patent
Sadeghi et al.

(10) Patent No.: US 10,597,340 B2
(45) Date of Patent: Mar. 24, 2020

(54) SYNTHESIS OF FLUORINATED RADIOPHARMACEUTICALS VIA ELECTROCHEMICAL FLUORINATION

(71) Applicant: The Regents of the University of California, Oakland, CA (US)

(72) Inventors: Saman Sadeghi, Los Angeles, CA (US); Qinggang He, Los Angeles, CA (US); Artem Lebedev, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 405 days.

(21) Appl. No.: 14/937,649

(22) Filed: Nov. 10, 2015

(65) Prior Publication Data

US 2016/0137567 A1     May 19, 2016

Related U.S. Application Data

(63) Continuation of application No. PCT/US2014/037731, filed on May 12, 2014.

(60) Provisional application No. 61/822,250, filed on May 10, 2013.

(51) Int. Cl.
| | |
|---|---|
| *A61K 51/04* | (2006.01) |
| *C07B 59/00* | (2006.01) |
| *C07C 37/62* | (2006.01) |
| *C07C 39/24* | (2006.01) |

(52) U.S. Cl.
CPC ............ *C07B 59/001* (2013.01); *A61K 51/04* (2013.01); *C07B 59/00* (2013.01); *C07C 37/62* (2013.01); *C07C 39/245* (2013.01); *C07B 2200/05* (2013.01)

(58) Field of Classification Search
CPC ......... A61K 51/00; A61K 51/04; C07B 59/00
See application file for complete search history.

(56) References Cited

U.S. PATENT DOCUMENTS

| | | | | |
|---|---|---|---|---|
| 7,087,681 | B2 * | 8/2006 | Umemoto ............... | C08F 2/58 525/332.1 |
| 2012/0123120 | A1 | 5/2012 | Satyamurthy et al. | |

FOREIGN PATENT DOCUMENTS

| | | |
|---|---|---|
| WO | WO-2009/073273 A2 | 6/2009 |
| WO | WO-2009/073273 A3 | 6/2009 |

OTHER PUBLICATIONS

G. Reischl et al., Electrochemical radiofluorination. Part 2. Anodic monofluorination of substituted benzenes using [18F]fluoride, Applied Radiation and Isotopes, 2003, 58, 679-683.*
G. Reischl et al. Electrochemical radiofluorination: Labeling of benzene with [18F]fluoride by nucleophilic substitution, 254(2), 409-411 (Year: 2002).*
Gabriele J. Kienzle et al., Electrochemical radiofluorination. 3. Direct labeling of phenylalanine derivatives with [18F]fluoride after anodic oxidation, J. Labeled Comp. Radiopharma, 48, 259-273. (Year: 2005).*
Anbarasan, P. et al. (2010). "Efficient synthesis of aryl fluorides," *Angewandte Chemie* 122:2265-2268.
Belding, S.R. et al. (2008). "Behavior of the Heterogeneous Electron-Transfer Rate Constants of Arenes and Substituted Anthracenes in Room-Temperature Ionic Liquids," *Journal of Physical Chemistry C* 112(5):1650-1657.
Block D. et al (Sep. 1987). "The N.C.A. nucleophilic $^{18}$F-fluorination of 1,N-disubstituted alkanes as fluoroalkylation agents," *Journal of Labelled Compounds and Radiopharmaceuticals* 24(9):1029-1042.
Coenen, H.H. et al (2010). "Direct Nucleophilic $^{18}$F-Fluorination of Electron Rich Arenes: Present Limits of No-Carrier-Added Reactions," *Current Radiopharmaceuticals* 3:163-173.
Fuchigami, T. et al. (Oct. 2011, e-published Jun. 25, 2011). "Selective electrochemical fluorination of organic molecules and macromolecules in ionic liquids," *Chem Commun (Camb)* 47(37):10211-10223.
Guo, N. et al. (Oct. 2008, e-published Mar. 10, 2008). "Microwave-induced nucleophilic [18F]fluorination on aromatic rings: synthesis and effect of halogen on [18F]fluoride substitution of meta-halo (F, Cl, Br, I)-benzonitrile derivatives," *Appl Radiat Isot* 66(10):1396-1402.
International Search Report dated Sep. 26, 2014, for PCT Application No. PCT/US2014/037731, filed May 12, 2014, 4 pages.
Jammaz, I et al. (2006). "Novel synthesis of [18F]-fluorobenzene and pyridinecarbohydrazide-folates as potential PET radiopharmaceuticals," *Journal of Labelled Compounds and Radiopharmaceuticals* 49:125-137.

(Continued)

*Primary Examiner* — Michael G. Hartley
*Assistant Examiner* — Jagadishwar R Samala
(74) *Attorney, Agent, or Firm* — Mintz, Levin, Cohn, Ferris, Glovsky and Popeo, P.C.; Irina E. Britva

(57) ABSTRACT

Provided herein are methods and compositions for the electrochemical selective radiofluorination of aromatic molecules. The resulting fluorine-18 labeled compounds are ideal radionuclides for use in Positron Emission Tomography (PET); they are also difficult to radiolabel efficiently and with high specific activity using existing approaches. For example, radiopharmaceuticals such as [F18]L-DOPA, which is indispensable in PET brain disease imaging, may be made electrochemically with high radiochemical yield and high specific activity using 18F-. The invention process described herein opens new possibilities and provides wider access to PET tracers such as 18F-L-Dopa, since 18F- is much more widely available than the $18F_2$, currently used for synthesis of electron rich substrates.

11 Claims, 3 Drawing Sheets

(56) References Cited

OTHER PUBLICATIONS

Kienzle, G.J. et al. (Feb. 10, 2005). "Electrochemical radiofluorination. 3. Direct labeling of phenylalanine derivatives with [$^{18}$F]fluoride after anodic oxidation," *Journal of Labelled Compounds and Radiopharmaceuticals* 48(4):259-273.

Lee, E. et al. (Nov. 4, 2011). "A fluoride-derived electrophilic late-stage fluorination reagent for PET imaging," *Science* 334(6056):639-642.

Namavari. M. et al. (Aug. 1992). "Regioselective radiofluorodestannylation with [$^{18}$F]F$_2$ and [$^{18}$F]CH$_3$COOF: A high yield synthesis of 6-[$^{18}$F]fluoro-l-dopa," *Applied Radiation and Isotopes* 43(8):989-996.

Written Opinion dated Sep. 26, 2014, for PCT Application No. PCT/US2014/037731, filed May 12, 2014, 8 pages.

\* cited by examiner

SYNTHESIS OF FLUORINATED RADIOPHARMACEUTICALS VIA ELECTROCHEMICAL FLUORINATION

CROSS-REFERENCE TO RELATED APPLICATION

This patent application claims priority to U.S. Provisional Patent Application No. 61/822,250, entitled "Synthesis of Fluorinated Radiopharmaceuticals via Electrochemical Fluorination," filed May 10, 2013, which is hereby incorporated by reference in its entirety for all purposes.

STATEMENT OF GOVERNMENT SUPPORT

This invention was made with Government support awarded by the U.S. Department of Energy. The Government has certain rights in this invention.

FIELD OF THE INVENTION

Provided herein are methods and compositions for the fluorination of aromatic compounds. In particular aspects and embodiments, the methods and compositions facilitate the preparation of fluorinated radiopharmaceutical compounds.

BACKGROUND OF THE INVENTION

The following description is provided to assist the understanding of the reader. None of the information provided or references cited is admitted to be prior art in the present invention.

Radiotracers of high specific activity are desirable for medical imaging with positron emission tomography (PET). $^{18}$F-labelled aromatic molecules of PET tracers can be synthesized via two common but direct pathways: electrophilic reactions (Lee E, et al (2011)Science, 334, 639-642) and nucleophilic substitution (Block D, et al (1987) Journal of Labelled Compounds and Radiopharmaceuticals, 24, 1029-1042; Guo N, et al (2008) Applied Radiation and Isotopes, 66, 1396-1402). Although direct electrophilic $^{18}$F-fluorination has been well established, this route has a number of drawbacks such as synthesis with fluorine gas, low radiochemical yield and low specific activity. As a result, development of a method with the ability to conduct $^{18}$F-fluorination of aromatic molecules through direct nucleophilic substitution is highly desirable.

The importance of fluorinated compounds in agrochemical, pharmaceutical and materials chemistry is well recognized. Furthermore, the radioisotope of fluorine (fluorine-18 ($^{18}$F)) is an ideal radionuclide for use in Positron Emission Tomography (PET) due to its ideal half-life of 110 minutes, while sufficient to allow for the multi-step synthesis of complex radiotracers and short enough to be safe for in-vivo clinical use. There are two sources of $^{18}$F available, the electrophilic agent [$^{18}$F]F$_2$ (and derivatives thereof) and the nucleophilic agent [$^{18}$F]fluoride. [$^{18}$F]F$_2$ is not as readily accessible and its production is carrier-added, decreasing the specific activity of resultant tracers. One of the limitations in use of [$^{18}$F]-fluoride for PET imaging is that there are currently very few methods for its introduction into organic molecules, restricting the design of new radiotracers. The majority of existing methods for the incorporation of $^{18}$F proceed via nucleophilic substitution reactions. When possible, these displacement reactions are efficient, allowing for the synthesis of radiotracers in high specific activity and good radiochemical yields. However, the nature of this transformation introduces severe structural constraints in the design of the radiotracer and limits the possibility of PET probes.

A number of important radiopharmaceuticals have structures that are not readily amenable to traditional nucleophilic fluorination. In particular, the high electron density of arenes make them energetically unfavorable for nucleophilic addition of fluorine anion. Decreasing the electron density of the substrate via an oxidized intermediate can be an effective method for promoting nucleophilic fluorination of aromatic molecules. In principle, it is possible to introduce [18F] fluoride via nucleophilic substitution by activating aromatic compounds using a strong electron withdrawing group. However, the commonly used approaches for nucleophilic fluorination of aromatic molecules need multiple steps to bring activation and leaving groups and subsequent elimination of these groups after the introduction of [18F]fluoride, which are extremely time-consuming and lead to dramatic decay of the radioactivity of fluorinated compounds. Forming labile intermediates can increase the repertoire of radiochemical reactions applicable to small and electron rich molecules. There are also prior reports on the fluorination of aromatics such as benzene and catechol derivatives, utilizing acetonitrile solution of Et$_3$N—HF as supporting electrolyte and source of fluoride.

SUMMARY OF THE INVENTION

Provided herein are methods and compositions for the electrochemical selective radiofluorination of aromatic molecules. The resulting fluorine-18 labeled compunds are ideal radionuclides for use in Positron Emission Tomography (PET); they are also difficult to radiolabel efficiently and with high specific activity using existing approaches. For example, radiopharmaceuticals such as [F18]L-DOPA, which is indispensable in PET brain disease imaging, may be made electrochemically with high radiochemical yield and high specific activity using 18F-. The invention process described herein opens new possibilities and provides wider access to PET tracers such as 18F-L-Dopa, since 18F- is much more widely available than the 18F$_2$, currently used for synthesis of electron rich substrates.

Among the methods to generate an electron-poor carbon in arenes, the electrochemical anodic oxidation is the most technically elegant because the reactions can be carried out under mild conditions and there is no hazardous chemical oxidant and reductant required. Different from other strategies, the oxidation effect can be precisely controlled by the applied potential on the working electrode. The accurate control is provided by the direct relation of electron density and redox potential for different carbon atoms with various substituents on the benzene ring.

Beside the common benefits of nucleophilic substitution, the electrochemical fluorination method has distinct advantages, important for radiopharmaceuticals such as L-DOPA and other complex aromatic compounds. Particularly, the fluorination reaction can be achieved in a non-carrier added fashion. Furthermore, potential simplification in the design of electrochemical precursors, as compared to traditional methods, incorporating strong electron withdrawing groups, use of chemical oxidants or organometallic synthesis methods, means electrochemical fluorination can benefit from reduced steric hindrance, practical handling of precursors, compatibility with simpler synthesis platforms and hence better yields in a practical setting. Lastly the delicate control of oxidation potential makes it feasible to achieve selective radiofluorination.

DETAILED DESCRIPTION OF THE INVENTION

Figure 1:
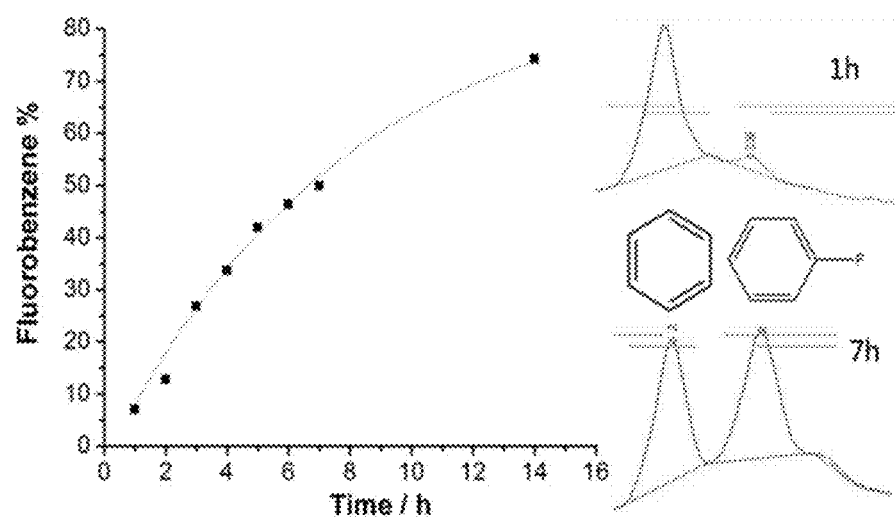
FIG. 1 presents HPLC results of electrochemical fluorination of benzene.

In accordance with the present invention, there are provided mixtures comprising an electrolyte, a [$^{18}F$] fluoride source, and a compound of the formula:

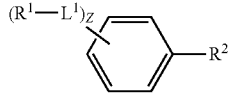

wherein,
z is an integer from 0 to 10;
$L^1$ is independently —O—, —NH—, —S—, —C(O)NH—, —NHC(O)—, —NHNH—, —S(O)—, —S(O)$_2$—, —ONH—, or —NHO—;
$R^1$ is independently hydrogen, halogen, —N$_3$, —CF$_3$, —CCl$_3$, —CBr$_3$, —CI$_3$, —CN, —C(O)R$^{3A}$, —OR$^{3A}$, —NR$^{3A}$R$^{3B}$, —C(O)OR$^3$, —CONR$^{3A}$R$^{3B}$, —NR$^{3A}$R$^{3B}$C(O)R$^{3C}$, —NO$_2$, —SR$^{3A}$, —SO$_2$, —SO$_2$Cl, —SO$_3$R$^{3A}$, —SO$_2$NR$^{3A}$R$^{3B}$, —NHNR$^{3A}$R$^{3B}$, —ONR$^{3A}$R$^{3B}$, —NHC(O)NHR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
$R^2$ is an electron donating leaving group; and
$R^{3A}$, $R^{3B}$ and $R^{3C}$ are independently hydrogen, halogen, —N$_3$, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein two $R^1$ subsitutents are optionally joined to from a substituted or unsubstituted cycloalkyl, substituted or unsubstituted heterocycloalkyl, substituted or unsubstituted aryl, or substituted or unsubstituted heteroaryl.

As used herein, the term "acyl" denotes the group —C(O)R$^a$, where R$^a$ is hydrogen, lower alkyl, cycloalkyl, heterocyclyl, aryl, heteroaryl, and the like.

As used herein, the term "substituted acyl" denotes the group —C(O)R$^{a'}$, where R$^{a'}$ is substituted lower alkyl, substituted cycloalkyl, substituted heterocyclyl, substituted aryl, substituted heteroaryl, and the like.

As used herein, the term "acyloxy" denotes the group —OC(O)R$^b$, where R$^b$ is hydrogen, lower alkyl, substituted lower alkyl, cycloalkyl, substituted cycloalkyl, heterocyclyl, substituted heterocyclyl, aryl, substituted aryl, heteroaryl, substituted heteroaryl, and the like.

As used herein, the term "alkane" refers to an organic compound that includes carbon atoms and hydrogen atoms, and includes C—H bonds and additionally includes C—C single bonds in alkanes other than methane. The term "alkane" includes straight-chain alkanes such as alkanes having from 1 to 20 carbon atoms. In some embodiments, alkanes include straight-chain alkanes such as alkanes having from 1 to 8 carbon atoms such as methane, ethane, propane, butane, pentane, hexane, heptane, and octane. The term "alkane" also includes branched-chain alkanes such as, but not limited to branched chain alkanes having from 1 to 20, and in some embodiments from 1 to 8 carbon atoms such as, but not limited to, 2-methylpropane, 2,2-dimethylpropane, 2-methylbutane, 2,3-dimethylbutane, 2,2-dimethylbutane, 2-methylpentane, 3-methylpentane, 2,3-dimethylpentane, 2,4-dimethylpentane, 2,2-dimethylpentane, 3,3-dimethylpentane, 2-methylhexane, 3-methylhexane, 2,2-dimethylhexane, 2,3-dimethylhexane, 2,4-dimethylhexane, 2,5-dimethylhexane, 3,3-dimethylhexane, 3,4-dimethylhexane, 2-methylheptane, 3-methylheptane, 4-methylheptane, 3-ethylpentane, 3-ethyl-2-methylpentane, 3-ethylhexane, and the like. A C—C or a C—H bond of an alkane may be replaced with a bond to another group such as a hydroxyl group, a halogen such as F, Cl, Br, or I, a sulfhydryl group, or an amine group. Alkanes replaced with such groups may respectively be named as hydroxyalkanes, haloalkanes such as fluoroalkanes, chloroalkanes, bromoalkanes, iodoalkanes, mercaptoalkanes, and aminoalkanes.

As used herein, the term "alkenyl" refers to a straight-chain or branched-chain hydrocarbyl, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

As used herein, the term "alkenylaryl" refers to alkenyl-substituted aryl groups and "substituted alkenylaryl" refers to alkenylaryl groups further bearing one or more substituents as set forth herein.

As used herein, the term "alkenylene" refers to divalent straight or branched chain hydrocarbyl groups having at least one carbon-carbon double bond, and typically containing 2-20 carbon atoms, preferably 2-12 carbon atoms, preferably 2-8 carbon atoms, and "substituted alkenylene" refers to alkenylene groups further bearing one or more substituents as set forth herein.

As used herein, the term "alkyl" refers to a single bond chain of hydrocarbons usually ranging from 1-20 carbon atoms, preferably 1-8 carbon atoms, examples include methyl, ethyl, propyl, isopropyl, and the like. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

As used herein, the term "lower alkyl" refers to a straight chain or a branched chain of hydrocarbons usually ranging from 1-6 carbon atoms, preferably 2-5 carbon atoms. Examples include ethyl, propyl, isopropyl, and the like.

As used herein, the term "alkylene" refers to a divalent hydrocarbyl containing 1-20 carbon atoms, preferably 1-15 carbon atoms, straight chain or branched, from which two hydrogen atoms are taken from the same carbon atom or from different carbon atoms. Examples of alkylene include, but are not limited to, methylene (—CH$_2$—), ethylene (—CH$_2$CH$_2$—), and the like.

As used herein, the term "alkynyl" refers to a straight-chain or branched-chain hydrocarbyl, which has one or more triple bonds and contains from about 2-20 carbon atoms, preferably from about 2-10 carbon atoms, more preferably from about 2-8 carbon atoms, and most preferably from about 2-6 carbon atoms. Examples of alkynyl radicals include ethynyl, propynyl (propargyl), butynyl, and the like.

As used herein, the term "alkynylaryl" refers to alkynyl-substituted aryl groups and "substituted alkynylaryl" refers to alkynylaryl groups further bearing one or more substituents as set forth herein.

As used herein, the term "alkoxy" denotes the group —OR$^c$, where R$^c$ is lower alkyl, substituted lower alkyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

As used herein, the term "lower alkoxy" denotes the group —OR$^d$, where R$^d$ is lower alkyl.

As used herein, the term "alkylaryl" refers to alkyl-substituted aryl groups and "substituted alkylaryl" refers to alkylaryl groups further bearing one or more substituents as set forth herein.

As used herein, the term "alkylcarbonylamino" denotes the group —NR$^e$C(O)R$^f$, where R$^e$ is optionally substituted alkyl, and R$^f$ is hydrogen or alkyl.

As used herein, the term "alkylsulfinyl" denotes the group —S(O)R$^g$, where R$^g$ is optionally substituted alkyl.

As used herein, the term "alkylsulfonyl" denotes the group —S(O)$_2$R$^g$, where R$^g$ is optionally substituted alkyl.

As used herein, the term "alkylsulfonylamino" denotes the group —NR$^e$S(O)$_2$R$^f$, where R$^e$ is optionally substituted alkyl, and R$^f$ is hydrogen or alkyl.

As used herein, the term "alkylthio" refers to the group —S—R$^h$, where R$^h$ is alkyl.

As used herein, the term "substituted alkylthio" refers to the group —S—R$^i$, where R$^i$ is substituted alkyl.

As used herein, the term "alkynylene" refers to divalent straight or branched chain hydrocarbyl groups having at least one carbon—carbon triple bond, and typically having in the range of about 2-12 carbon atoms, preferably about 2-8 carbon atoms, and "substituted alkynylene" refers to alkynylene groups further bearing one or more substituents as set forth herein.

As used herein, the term "amido" denotes the group —C(O)NR$^j$R$^{j'}$, where R$^j$ and R$^{j'}$ may independently be hydrogen, lower alkyl, substituted lower alkyl, alkyl, substituted alkyl, aryl, substituted aryl, heteroaryl, or substituted heteroaryl.

As used herein, the term "substituted amido" denotes the group —C(O)NR$^k$R$^{k'}$, where R$^k$ and R$^{k'}$ are independently hydrogen, lower alkyl, substituted lower alkyl, aryl, substituted aryl, heteroaryl, or substituted heteroaryl, provided, however, that at least one of R$^k$ and R$^{k'}$ is not hydrogen. R$^k$R$^{k'}$ in combination with the nitrogen may form an optionally substituted heterocyclic or heteroaryl ring.

As used herein, the term "amidino" denotes the group —C(=NR$^m$)NR$^{m'}$R$^{m''}$, where R$^m$, R$^{m'}$, and R$^{m''}$ are independently hydrogen or optionally substituted alkyl, aryl, or heteroaryl.

As used herein, the term "amino" or "amine" denotes the group —NR$^n$R$^{n'}$, where R$^n$ and R$^{n'}$ may independently be hydrogen, lower alkyl, substituted lower alkyl, alkyl, substituted alkyl, aryl, substituted aryl, heteroaryl, or substituted heteroaryl as defined herein. A "divalent amine" denotes the group —NH—. A "substituted divalent amine" denotes the group —NR— where R is lower alkyl, substituted lower alkyl, alkyl, substituted alkyl, aryl, substituted aryl, heteroaryl, or substituted heteroaryl.

As used herein, the term "substituted amino" or "substituted amine" denotes the group —NR$^p$R$^{p'}$, where R$^p$ and R$^{p'}$ are independently hydrogen, lower alkyl, substituted lower alkyl, alkyl, substituted alkyl, aryl, substituted aryl, heteroaryl, substituted heteroaryl, provided, however, that at least one of R$^p$ and R$^{p'}$ is not hydrogen. R$^p$R$^{p'}$ in combination with the nitrogen may form an optionally substituted heterocyclic, or heteroaryl ring.

As used herein, the term "arylalkynyl" refers to aryl-substituted alkynyl groups and "substituted arylalkynyl" refers to arylalkynyl groups further bearing one or more substituents as set forth herein.

As used herein, the term "aralkyl" refers to alkyl as defined herein, where an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

As used herein, the term "aroyl" refers to aryl-carbonyl species such as benzoyl and "substituted aroyl" refers to aroyl groups further bearing one or more substituents as set forth herein.

As used herein, the term "arylalkyl" refers to aryl-substituted alkyl groups and "substituted arylalkyl" refers to arylalkyl groups further bearing one or more substituents as set forth herein.

As used herein, the term "aryl" alone or in combination refers to phenyl, naphthyl or fused aromatic heterocyclic optionally with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

As used herein, the term "arylcarbonylamino" denotes the group —NR$^q$C(O)R$^r$, wherein R$^q$ is hydrogen or lower alkyl or alkyl and R$^r$ is optionally substituted aryl.

As used herein, the term "arylene" refers to divalent aromatic groups typically having in the range of 6 up to 14 carbon atoms and "substituted arylene" refers to arylene groups further bearing one or more substituents as set forth herein.

As used herein, the term "aryloxy" denotes the group —OAr, where Ar is an aryl, or substituted aryl group.

As used herein, the term "arylsulfonylamino" denotes the group —NR$^q$S(O)$_2$R$^r$, where R$^q$ is hydrogen or lower alkyl, or alkyl and R$^r$ is optionally substituted aryl.

As used herein, the term "a carbamate group" denotes the group —O—C(O)—NR$_2$, where each R is independently H, alkyl, substituted alkyl, aryl, or substituted aryl as set forth herein.

As used herein, the term "dithiocarbamate group" denotes the group —S—C(S)—NR$_2$, where each R is independently H, alkyl, substituted alkyl, aryl, or substituted aryl as set forth herein.

As used herein, the term "carbocycle" refers to a saturated, unsaturated, or aromatic group having a single ring or multiple condensed rings composed of linked carbon atoms. The ring(s) can optionally be unsubstituted or substituted with, e.g., halogen, lower alkyl, alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "cycloalkenyl" refers to cyclic ring-containing groups containing in the range of 3-20 carbon atoms and having at least one carbon-carbon double bond, and "substituted cycloalkenyl" refers to cycloalkenyl groups further bearing one or more substituents as set forth herein.

As used herein, the term "cycloalkyl" refers to a monocyclic or polycyclic alkyl group containing 3-15 carbon atoms, and "substituted cycloalkyl" refers to cycloalkyl groups further bearing one or more substituents as set forth herein.

As used herein, the term "cycloalkylene" refers to divalent ring-containing groups containing in the range of about 3-12 carbon atoms, and "substituted cycloalkylene" refers to cycloalkylene groups further bearing one or more substituents as set forth herein.

As used herein, the term "guanidinyl" denotes the group $-N=C(NH_2)_2$ and "substituted guanidinyl" denotes the group $-N=C(NR_2)_2$, where each R is independently H, alkyl, substituted alkyl, aryl, or substituted aryl as set forth herein.

As used herein, the term "halo" or "halogen" refers to all halogens, i.e., chloro (Cl), fluoro (F), bromo (Br), and iodo (I).

As used herein, the term "heteroaryl" refers to a monocyclic aromatic ring structure containing 5 or 6 ring atoms, or a bicyclic aromatic group having 8-10 atoms, containing one or more, preferably 1-4, more preferably 1-3, even more preferably 1-2 heteroatoms independently selected from the group O, S, and N, and optionally substituted with 1-3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl, or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl, and N-oxide of a tertiary ring nitrogen. A carbon or nitrogen atom is the point of attachment of the heteroaryl ring structure such that a stable aromatic ring is retained. Examples of heteroaryl groups are phthalimide, pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like. A substituted heteroaryl contains a substituent attached at an available carbon or nitrogen to produce a stable compound.

As used herein, the term "substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

As used herein, the term "heteroarylcarbonylamino" denotes the group $-NR^qC(O)R^r$, where $R^q$ is hydrogen or lower alkyl, and $R^r$ is optionally substituted aryl.

As used herein, the term "heteroaryloxy" denotes the group —OHet, where Het is an optionally substituted heteroaryl group.

As used herein, the term "heteroarylsulfonylamino" denotes the group $-NR^qS(O)_2R^s$, where $R^q$ is hydrogen or lower alkyl and $R^s$ is optionally substituted heteroaryl.

As used herein, the term "heterocycle" refers to a saturated, unsaturated, or aromatic group having a single ring (e.g., morpholino, pyridyl or furyl) or multiple condensed rings (e.g., naphthpyridyl, quinoxalyl, quinolinyl, indolizinyl or benzo[b]thienyl) and having carbon atoms and at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "substituted heterocycle" refers to a heterocycle substituted with 1 or more, e.g., 1, 2, or 3, substituents selected from the group consisting of optionally substituted alkyl, optionally substituted alkenyl, optionally substituted alkynyl, halo, hydroxy, alkoxy, alkylthio, alkylsulfinyl, alkylsulfonyl, acyloxy, aryl, substituted aryl, aryloxy, heteroaryloxy, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, acyl, carboxyl, heterocycle, substituted heterocycle, hetaryl, substituted hetaryl, nitro, cyano, thiol, sulfonamido, and oxo, attached at any available point to produce a stable compound.

As used herein, the term "hydrocarbyl" refers to any organic radical where the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like.

As used herein, the term "substituted hydrocarbyl" refers to any of the above-referenced hydrocarbyl groups further bearing one or more substituents selected from hydroxy, hydrocarbyloxy, substituted hydrocarbyloxy, alkylthio, substituted alkylthio, arylthio, substituted arylthio, amino, alkylamino, substituted alkylamino, carboxy, —C(S)SR, —C(O)SR, —C(S)NR$_2$, where each R is independently hydrogen, alkyl or substituted alkyl, nitro, cyano, halo, —SO$_3$M or —OSO$_3$M, where M is H, Na, K, Zn, Ca, or meglumine, guanidinyl, substituted guanidinyl, hydrocarbyl, substituted hydrocarbyl, hydrocarbylcarbonyl, substituted hydrocarbylcarbonyl, hydrocarbyloxycarbonyl, substituted hydrocarbyloxycarbonyl, hydrocarbylcarbonyloxy, substituted hydrocarbylcarbonyloxy, acyl, acyloxy, heterocyclic, substituted heterocyclic, heteroaryl, substituted heteroaryl, heteroarylcarbonyl, substituted heteroarylcarbonyl, carbamoyl, monoalkylcarbamoyl, dialkylcarbamoyl, arylcarbamoyl, a carbamate group, a dithiocarbamate group, aroyl, substituted aroyl, organosulfonyl, substituted organosulfonyl, organosulfinyl, substituted alkylsulfinyl, alkylsulfonylamino, substituted alkylsulfonylamino, arylsulfonylamino, substituted arylsulfonylamino, a sulfonamide group, sulfuryl, and the like, including two or more of the above-described groups attached to the hydrocarbyl moiety by such linker/spacer moieties as —O—, —S—, —NR—, where R is hydrogen, alkyl or substituted alkyl, —C(O)—, —C(S)—, —C(=NR')—, —C(=CR'$_2$)—, where R' is alkyl or substituted alkyl, —O—C(O)—, —O—C(O)—O—, —O—C (O)—NR—(or —NR—C(O)—O—), —NR—C(O)—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S) —NR—, —NR—O—C(S)—, —NR—O—C(S)—O—, —NR—O—C(S)—NR—, —O—C(S)—, —O—C(S)—O—, —O—C(S)—NR—(or —NR—C(S)—O—), —NR—C(S)—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—, where each R is independently hydrogen, alkyl or substituted alkyl, and the like.

As used herein, the term "hydrocarbyloxy" denotes —O—hydrocarbyl groups containing 2-20 carbon atoms and "substituted hydrocarbyloxy" refers to hydrocarbyloxy groups further bearing one or more substituents as set forth herein.

As used herein, the term "hydrocarbylcarbonyl" refers to —C(O)-hydrocarbyl groups containing 2-20 carbon atoms and "substituted hydrocarbylcarbonyl" refers to hydrocarbylcarbonyl groups further bearing one or more substituents as set forth herein.

As used herein, the term "hydrocarbyloxycarbonyl" refers to —C(O)—O-hydrocarbyl containing 2-20 carbon atoms and "substituted hydrocarbyloxycarbonyl" refers to hydrocarbyloxycarbonyl groups further bearing one or more substituents as set forth herein.

As used herein, the term "hydrocarbylcarbonyloxy" refers to —O—C(O)-hydrocarbyl groups 2-20 carbon atoms and "substituted hydrocarbylcarbonyloxy" refers to hydrocarbylcarbonyloxy groups further bearing one or more substituents as set forth herein.

As used herein, the term "hydrocarbylene" refers to any divalent organic radical wherein the backbone thereof comprises carbon and hydrogen only. Thus, hydrocarbylene embraces alkylene, cycloalkylene, alkenylene, cycloalkenylene, alkynylene, arylene, alkylarylene, arylalkylene, arylalkenylene, alkenylarylene, arylalkynylene, alkynylarylene, and the like, and "substituted hydrocarbylene" refers to any of the above-referenced hydrocarbylene groups further bearing one or more substituents as set forth herein.

As used herein, the term "hydroxyl" or "hydroxy" refers to the group —OH.

As used herein, the term "organosulfinyl" denotes the group —S(O)-organo, where organo embraces alkyl-, alkoxy-, alkylamino-, and aryl moieties, as well as substituted alkyl-, alkoxy-, alkylamino-, and aryl moieties.

As used herein, the term "organosulfonyl" denotes the group —S(O)$_2$-organo, where organo embraces alkyl-, alkoxy- and alkylamino-moieties, as well as substituted alkyl-, alkoxy- or alkylamino-moieties.

As used herein, the term "oxo" refers to an oxygen substituent double bonded to the attached carbon.

As used herein, the term "sulfinyl" denotes the group —S(O)—.

As used herein, the term "substituted sulfinyl" denotes the group —S(O)R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonyl" denotes the group —S(O)$_2$—.

As used herein, the term "substituted sulfonyl" denotes the group —S(O)$_2$R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonylamino" denotes the group —NR$^q$S(O)$_2$— where R$^q$ is hydrogen or lower alkyl.

As used herein, the term "substituted sulfonylamino" denotes the group —NR$^q$S(O)$_2$R$^u$, where R$^q$ is hydrogen or lower alkyl and R$^u$ is lower alkyl, substituted lower alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl, or substituted aralkyl.

As used herein, the term "sulfuryl" denotes the group —S(O)$_2$—.

As used herein in connection with numerical values, the term "approximately" or "about" means 10% of the indicated value.

Nucleophilic substitution in aromatic compounds is highly unfavorable due to high electron density of the benzene ring. For the existing art, it is necessary to use F2 gas as a carrier to make electrophilic fluorination, which significantly decreases the radiochemical yield and specific activity and causes extensive purification and isolation. However, by means of electrochemisty, fluoride-18 can easily react with a phenylic carbenium ion formed by anodic oxidation. The electrode potentials can be tuned precisely according to the nature of the aromatic hydrocarbons, which minimizes the production of side products. Overall, the electrochemical radiofluorination of organic compounds can proceed under mild conditions with much higher efficiency, much higher radiochemical yield and specific activity.

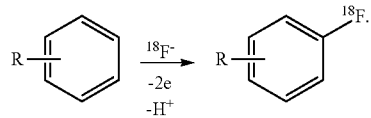

Electrochemical selective fluorination can be conducted in a variety of ways, e.g., in beaker cells, flow cells, and the like, with a Pt working electrode, a Pt counter electrode and an Ag/Ag$^+$ reference electrode. The potential for the electrochemical fluorination of a molecule can be chosen and precisely controlled according to the information from cyclic voltammetry measurement results. Generally, no concurrent oxidation of solvent or electrolyte salts should be seen during anodic oxidation of substrate molecules on some specific electrode materials. In addition, a pulsing technique by reversing the polarity of electrodes or switching the potential from a high level to a low level periodically can be used to minimize surface polymerization and poisoning issues. The fluorinated product can be purified and detected in a variety of ways, e.g., by standard HPLC, TLC and other methods. The electrochemical fluorination technique can further be applied to a number of other substrates.

In certain embodiments of the present invention, mixtures contemplated herein are carrier free. As used herein, "carrier free" refers to reaction media substantially lacking added $^{19}F$ species; such media are capable of fluorination of the target molecule; alternatively, such media are characterized as having a concentration of less than 1 mM $^{19}F$ species in the media. Carrier free media can be achieved in a variety of ways, e.g., by elution of $^{18}F$ species, previously absorbed on a solid support, using salts of organic carboxylic acids. Such salts can be comprised of cations (e.g., quaternary or tertiary ammonium or phosphonium ions, including but not limited to $Bu_4N^+$, $Et_4N^+$, $Et_3NH^+$, $Bu_4P^+$, $Et_4P^+$, $Ph_4P^+$, N,N'-dimethylimidazolium$^+$) and carboxylic anions (e.g., acetate, propionate, or any other alkanoic or cycloalaknoic acid anions, substituted or unsubstituted aromatic or heteroaromatic carboxylic acids). Exemplary salts include $NBu_4Ac$, $NBu_4OTos$, $NBu_4HSO_4$, $Et_3NHAc$, and the like.

In certain embodiments of the present invention, the mixtures described herein comprise one or more added carriers, e.g., wherein the concentration of all $^{19}F$ species capable of electrochemically mediated fluorination exceeds 1 mM. Exemplary carrier added mixtures comprise a molecule or an ion capable of interacting with other molecules in such a manner as to transfer an $^{19}F$ or $^{18}F$ atom upon absorbing same on a solid support. Examples include $^{19}F$-$Bu_4NF$, $^{19}F$-$Et_4NF$, $^{19}F$—F—, $^{19}F$—$HF_2^-$, $^{19}F$-$Et_3HF*3HF$, and the like.

In accordance with another embodiment of the present invention, there are provided methods of forming an [$^{18}F$] aryl fluoride compound, the method comprising:

contacting an [$^{18}F$] fluoride source with an aryl compound comprising a reactive aryl carbon covalently bound to an electron donating leaving group within an electrochemical mixture optionally comprising a solvent; and allowing said [$^{18}F$] fluoride source to react with said reactive aryl ring carbon in the presence of an applied electrical current thereby forming said [$^{18}F$]aryl fluoride compound.

In certain embodiments, the electrochemical mixture employed in the above-described method is a carrier free electrochemical mixture.

In other embodiments, the electrochemical mixture employed in the above-described method is a carrier added electrochemical mixture.

[$^{18}F$]aryl fluoride compounds contemplated for preparation by invention methods have the structure:

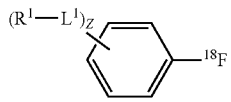

wherein, z is an integer from 0 to 10;

$L^1$ is independently —O—, —NH—, —S—, —C(O) NH—, —NHC(O)—, —NHNH—, —S(O)—, —S(O)$_2$—, —ONH—, or —NHO—;

$R^1$ is independently hydrogen, halogen, —N$_3$, —CF$_3$, —CCl$_3$, —CBr$_3$, —CI$_3$, —CN, —C(O)R$^{3A}$, —OR$^{3A}$, —NR$^{3A}$R$^{3B}$, —C(O)OR$^3$, —CONR$^{3A}$R$^{3B}$, —NR$^{3A}$R$^{3B}$C(O)R$^{3C}$, —NO$_2$, —SR$^{3A}$, —SO$_2$, —SO$_2$Cl, —SO$_3$R$^{3A}$, —SO$_2$NR$^{3A}$R$^{3B}$, —NHNR$^{3A}$R$^{3B}$, —ONR$^{3A}$R$^{3B}$, —NHC(O) NHR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and $R^{3A}$, $R^{3B}$ and $R^{3C}$ are independently hydrogen, halogen, —N$_3$, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein two $R^1$ subsitutents are optionally joined to from a substituted or unsubstituted cycloalkyl, substituted or unsubstituted heterocycloalkyl, substituted or unsubstituted aryl, or substituted or unsubstituted heteroaryl like.

In accordance with yet another embodiment of the present invention, there are provided methods of forming an [$^{18}F$] aryl fluoride compound, the methods comprising attaching a radioactive atom of fluorine to an aromatic compound by placing a mixture as described herein into an electrochemical cell and passing an effective amount of electrical current through said electrochemical mixture. As used herein, an "effective amount of electrical potential" refers to that potential which is sufficient to promote the desired electrochemical fluorination of a molecule. An effective amount can be chosen and precisely controlled according to information obtained from cyclic voltammetry measurement results. Generally, the electrical potential is selected so that no concurrent oxidation of solvent or electrolyte salts should be seen during anodic oxidation of substrate molecules on some specific electrode materials.

Exemplary electrical potentials contemplated for use herein are typically at least 1 V; in some embodiments, the electrical potential is at least 1.5 V; in some embodiments, the electrical potential is at least 2 V; in some embodiments, the electrical potential is at least 2.5 V; in some embodiments, the electrical potential is at least 3 V. In some embodiments, the electrical potential is no greater than 5 V; in some embodiments, the electrical potential is no greater than 4.5 V; in some embodiments, the electrical potential is no greater than 4 V; in some embodiments, the electrical potential is no greater than 3.5 V; in some embodiments, the electrical potential is no greater than 3 V.

In accordance with still another embodiment of the present invention, there are provided methods of attaching a radioactive atom of fluorine to an aromatic compound, thereby producing an [$^{18}F$]aryl fluoride compound, the method comprising placing a mixture as described herein into an electrochemical cell and controlling the potential for an appropriate period of time.

Fluorinated target molecules produced by invention methods, employing the mixtures described herein typically have excellent specific activities. For example, in certain embodiments, fluorinated compounds produced according to the invention have a specific activity of more than 13 GBq/μmol; in certain embodiments, fluorinated compounds produced according to the invention have a specific activity of more than 20 GBq/μmol; in certain embodiments, fluorinated compounds produced according to the invention have a specific activity of more than 43 GBq/μmol; in certain embodiments, fluorinated compounds produced according to the invention have a specific activity of more than 50 GBq/μmol.

As used herein, the term "gigabecquerel" (GBq) is a decimal multiple of the SI derived unit of radiation activity.

The Bq is defined as the activity of a quantity of radioactive material in which one nucleus decays per second. The becquerel is therefore equivalent to an inverse second, $s^{-1}$:

1 gigabecquerel [GBq]=27.027027027027 millicurie [mCi].

A millicurie (mCi) is a decimal fraction of the deprecated non-SI unit of radioactivity defined as 1 Ci=$3.7 \times 10^{10}$ decays per second. One curie is roughly the activity of 1 gram of the radium isotope $^{226}$Ra.

Precursors

A variety of aryl compounds can be used for fluorination according to the present invention, e.g., benzene, fluorobenzene, chlorobenzene, bromobenzene, iodobenzene, tert-butylbenzene, benzyltrimethlsilane, benzyl phenyl sulfide, diphenyl sulfide, diethylaniline. Additional aryl compounds contemplated for use herein include phenol, phenyl carbonate, tert-butyl phenyl carbonate, iodophenyl carbonate, and the like. Tert-butyl and tert-butyloxycarbonyl (BOC) can be used as leaving and protecting groups for producing fluorocatechol.

Electrode Materials

Electrode materials contemplated for use herein can be Pt, graphite or a gold working electrode. A Pt counter electrode and an Ag/Ag+ reference electrode can be used to successfully perform electrochemical fluorination of aromatic molecules. The $^{18}$F fluorine can be used directly from the cyclotron, following azeotropic drying and re-dissolving in an anhydrous solvent, (e.g. acetonitrile, dimethoxy ethane (DME)), through extraction from a solid phase extraction cartridge incorporating an ion-exchange resin.

Electrolyte and Solvent

Electrolytes contemplated for use herein include ionic salts comprised of a cation and an anion, wherein both are stable under the chosen electrolytic conditions. Exemplary cations include quaternary or tertiary ammonium or phosphonium ions, e.g., $Bu_4N^+$, $Et_4N^+$, $Et3NH^+$, $Bu_4P^+$, $Et_4P^+$, $Ph_4P^+$, N,N'-dimethylimidazolium$^+$, and the like; exemplary anions include stable anions with oxidation potential exceeding the oxidation potential chosen for the fluorination reaction, including but not limited to $ClO_4^-$, $PF_6^-$, $BF_4^-$, OTf$^-$, ONf$^-$, OTos$^-$, OMes$^-$, $HSO_4^-$, and the like; exemplary electrolytes include $NBu_4ClO_4$, $NBu_4PF_6$, and the like.

A wide variety of solvents can be employed in the preparation of invention mixtures. Any liquid which is capable of dissolving the other constituents of the mixture (while not undergoing any noticeable decomposition upon application of oxidation or reduction potential conducive to the electrolysis of the target compound) is suitable for use herein. Exemplary solvents include acetonitrile, dimethoxy ethane, N-Methylpyrrolidinone, dimethylaceatmide, and the like.

Successful electrochemical fluorination of aromatic molecules can be achieved in anhydrous acetonitrile containing triethylamine hydrofluoride. In addition, electrochemical fluorination of aromatic molecules can also occur with lower product yield using other fluorine sources such as TMAF, TEAF, TBAF, etc.

Operating Parameters

Electrochemical fluorination of aromatic molecules can be conducted under a constant potential control mode. A pulsing technique can be used to reverse the polarity of the working electrode periodically so as to minimize polymerization.

Among the methods to generate an electron-poor carbon in arenes as a prerequisite step for nucleophilic fluorination of aromatic molecules, the electrochemical anodic oxidation is probably the most elegant technically because the reactions can be carried out under mild conditions and there is no complex precursor required due to reduced number of synthetic steps. (Coenen H H, et al (2010) Current Radiopharmaceuticals3, 163-173; Fuchigami T, et al (2011) Chemical Communications 47, 10211-10223). As described herein, benzene is exemplary of the substrates that can be used to carry out electrochemical nucleophilic fluorination. Furthermore, nucleophilic substitution of intermediate molecules for PET probes can also be performed using potentiostatic anodic oxidation.

A Microflow Cell for Preparation of Fluorinated Products

From FIG. 1, benzene is shown to be labeled with F after being electrochemically oxidized on a Pt electrode for 7 h in $CH_3CN$ containing 0.6M $Et_3N$. 3HF as the electrolyte. Electrochemical operation parameters (e.g. pulsing potentials, frequency, electrolyte concentration) can be optimized based on results from electrochemical characterization techniques such as cyclic voltammetry and analytical methods for quality control such as HPLC and TLC.

Figure 2:
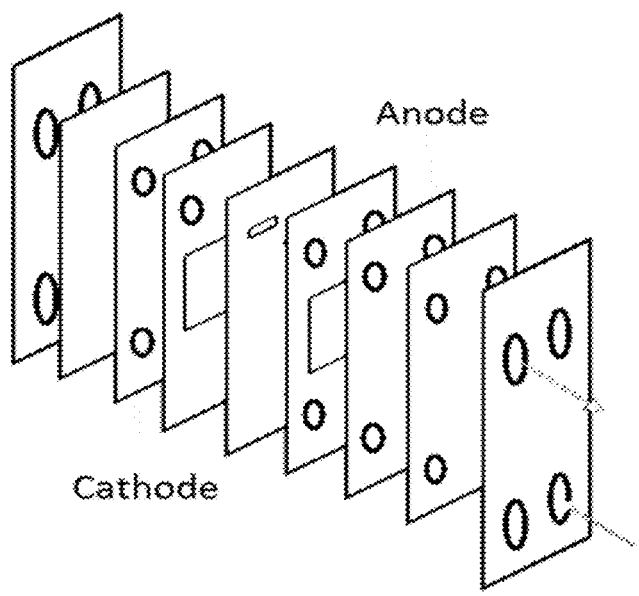
FIG. 2: presents a schematic of an electrochemical flow cell.

Electrolysis can be carried out using a single-compartment microflow-cell. A schematic illustration of an example microflow cell system is shown in FIG. 2. The microflow cell can be employed to improve the efficiency of the reactions and significantly reduce the reaction time. For example, for electrochemical fluorination of 4-Fluorophenol and 4-Fluorocatechol, several leaving groups at the 4 position and protecting groups for hydroxyl can be used. The results show that a precursor with an iodide leaving group and a tert-Butyloxycarbonyl (BOC) protecting group shows excellent product yield. Platinum sheets, carbon or gold foils can be used as anodic and cathodic electrodes. The flowing-in and flowing-out system can help improve the efficiency of radiofluorination. An L-shape Ag wire can be used as a pseudo-reference electrode, although incorporation of a Ag/Ag+ reference electrode is also possible.

A computer controlled platform can be employed to facilitate auxiliary processes, such as trapping of fluoride, release of fluoride into the reaction mixture, controlling of the flow, filling of the cell and product extraction.

Product Detection

Product detection can be achieved through TLC, HPLC and LCMS. A good mobile phase for detection of benzene and fluorobenzene by HPLC is a C18 column, mobile phase: 30% MeCN and 70% water, flow rate: 1.75 ml/min, wave length: 254 nm.

A good example of a mobile phase for detection of fluorocatechol by HPLC is a C18 column, mobile phase: 70% MeOH and 30% water, flow rate: 1.0 ml/min, wave length: 254 nm.

Removal of the electrolyte salt and other impurities after the electrochemical fluorination can be achieved though incorporation solid phase extraction cartridges. It has been found, for example, that Et3N. 3HF salt can be successfully removed by passing the solution through a silica cartridge and rinsing with THF or ethyl acetate, or through trapping of product on a reverse phase cartridge, washing away the polar impurities and subsequent elution of the product by ethanol or methanol. The purification method may be incorporated into the automated flow-through synthesizer.

Electrochemical Radiofluorination

Radiofluorination syntheses can be achieved by removal of water from [18F]fluoride through various solvent-exchange processes. An aqueous fluorination method may also be possible. Traditional azeotropic evaporation step usually causes the loss of activity associated with the drying and reconstitution of [18F]fluoride in a vial as well as its subsequent transfer to the microreactor. Alternatively, better results can be achieved with the use of anion exchange columns to extract 18F ions from water and their subsequent release by passing suitable salts in non-aqueous solutions. Supporting electrolytes can enable an electrochemical reaction, considering that 18F ion is in the nano molar concentration range, which is not sufficient to provide necessary conductivity for the electrochemical method. Exemplary stable salts with good solubility in organic solvents include tetrabutylammonium hexafluorophosphate, tetrabutylammonium methyl sulfate, bis(triphenylphosphoranylidence) ammonium tetrakis[3,5-bis(trifluoromethyl)phenyl]borate; in some embodiments, triethylamine hydrofluoride is a suitable stable salt for this purpose.

In accordance with another embodiment of the present invention, there are provided mixtures comprising a solvent, an electrolyte, a [$^{18}$F] fluoride source, and a compound of the formula:

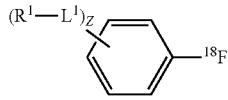

wherein,
z is an integer from 0 to 10;
$L^1$ is independently —O—, —NH—, —S—, —C(O)NH—, —NHC(O)—, —NHNH—, —S(O)—, —S(O)$_2$—, —ONH—, or —NHO—;
$R^1$ is independently hydrogen, halogen, —N$_3$, —CF$_3$, —CCl$_3$, —CBr$_3$, —CI$_3$, —CN, —C(O)R$^{3A}$, —OR$^{3A}$, —NR$^{3A}$R$^{3B}$, —C(O)OR$^3$, —CONR$^{3A}$R$^{3B}$, —NR$^{3A}$R$^{3B}$C(O)R$^{3C}$, —NO$_2$, —SR$^{3A}$, —SO$_2$, —SO$_2$Cl, —SO$_3$R$^{3A}$, —SO$_2$NR$^{3A}$R$^{3B}$, —NHNR$^{3A}$R$^{3B}$, —ONR$^{3A}$R$^{3B}$, —NHC(O)NHR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^{3A}$, $R^{3B}$ and $R^{3C}$ are independently hydrogen, halogen, —N$_3$, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein two $R^1$ subsitutents are optionally joined to from a substituted or unsubstituted cycloalkyl, substituted or unsubstituted heterocycloalkyl, substituted or unsubstituted aryl, or substituted or unsubstituted heteroaryl.

Optionally, the above-described mixture further comprises an electron donating leaving group product, i.e., the electron donating leaving group as it exists after leaving and forming a stable compound in the mixture; alternatively, electron donating leaving group products include a combination of atoms increasing electron density on the aromatic ring and capable of forming a stable cation when detached from the aromatic ring. Exemplary embodiments include tertiary alkyl groups (e.g., tertiary butyl), trialkylsilyl radicals (e.g., trimethylsilyl), trialkyl stannyl radicals (e.g., trimethylstannyl), or other stabilized cations such as, for example, isobutylene and products of its polymerization, tertbutylfluoride, tertbutyl acetate, tertbutyl alcohol, tertbutylacetamide, trimetylsilylfluoride, trimethylstannylfluoride, and the like.

In certain embodiments, mixtures according to the present invention are anhydrous, i.e., substantially free of water.

In certain embodiments of the present invention, the above-described mixtures form part of an electrochemical cell. In certain embodiments of the present invention, the above-described electrochemical cell comprises a potentiostat.

Electrochemical cells contemplated for use herein comprise an electrode made of a suitable metal or alloy of metals. Exemplary electrodes are made of Pt, Pd, Au, Ni, Rh, Re, Ta, Ti, and the like, as well as combinations of any 2 or more thereof.

In accordance with yet another embodiment of the present invention, there are provided mixtures comprising a solvent, an electrolyte and a compound of the formula:

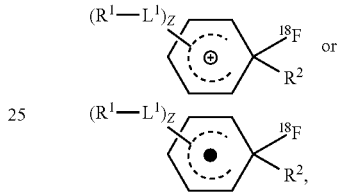

wherein,
z is an integer from 0 to 10;
$R^2$ is an electron donating leaving group;
$L^1$ is independently —O—, —NH—, —S—, —C(O)NH—, —NHC(O)—, —NHNH—, —S(O)—, —S(O)$_2$—, —ONH—, or —NHO—;
$R^1$ is independently hydrogen, halogen, —N$_3$, —CF$_3$, —CCl$_3$, —CBr$_3$, —CI$_3$, —CN, —C(O)R$^{3A}$, —OR$^{3A}$, —NR$^{3A}$R$^{3B}$, —C(O)OR$^3$, —CONR$^{3A}$R$^{3B}$, —NR$^{3A}$R$^{3B}$C(O)R$^{3C}$, —NO$_2$, —SR$^{3A}$, —SO$_2$, —SO$_2$Cl, —SO$_3$R$^{3A}$, —SO$_2$NR$^{3A}$R$^{3B}$, —NHNR$^{3A}$R$^{3B}$, —ONR$^{3A}$R$^{3B}$, —NHC(O)NHR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and
$R^{3A}$, $R^{3B}$ and $R^{3C}$ are independently hydrogen, halogen, —N$_3$, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
wherein two $R^1$ subsitutents are optionally joined to form a substituted or unsubstituted cycloalkyl, substituted or unsubstituted heterocycloalkyl, substituted or unsubstituted aryl, or substituted or unsubstituted heteroaryl.

The methods and compositions provided herein will now be described in greater detail by reference to the following non-limiting examples.

EXAMPLE 1

Theoretical Studies

All Density Functional Theory (DFT) calculations were carried out with the Jaguar 7.6 program package by Schrödinger LLC. For geometry optimizations, solvation energy, and frequency calculations, Becke's three-parameter hybrid functional and the LYP correlation functional (B3LYP)(Becke, 1993; Lee et al., 1988) was used with the 6-311G++basis set. Frequency calculations were performed on the optimized geometries to verify that the geometries correspond to minima on the potential energy surface (PES). The Gibbs free energies were defined as the following equation G=E (B3LYP/6-311G++)+$G_{solv}$+ZPE+$H_{298}$ −$TS_{298}$. The solvation model applied (in acetonitrile) was the Poisson -Bolzmann reactive field implemented in Jaguar 7.6 (PBF).(Marten et al., 1996) All potential values were given vs. NHE (normal hydrogen electrode).

EXAMPLE 2

Chemicals

HPLC grade acetonitrile (MeCN) and anhydrous phorsphorus pentaoxide ($P_2O_5$) were purchased from Fisher Scientific and distilled over $CaH_2$ to prepare the anhydrous solvent. Triethylamine trihydrofluoride ($Et_3N.3HF$), tetrabutylammonium perchlorate ($NBu_4ClO_4$) and tetrabutylammonium hexafluorophosphate ($NBu_4PF_6$) were ordered from Sigma-Aldrich and used as received. To conduct radiofluorination of catechol, Boc protection was used to protect the hydroxyl function on the aromatic ring. 4-tert-butyl-1,2-catechol (3.0 g, 0.018 mol) was dissolved in 20 mL of anhydrous dichloromethane. The solution was cooled down in an ice bath. Triethylamine (21.8 g, 0.216 mol) was added drop wise to the cooled solution. After completion of the addition, di-tert-butyl dicarbonate (15.4 ml, 0.072 mol) was added drop wise to the resulting solution. The reaction mixture was then stirred at room temperature overnight. The reaction was quenched with 100 mL of water. The aqueous layer was extracted with dichloromethane (3×50 mL) after layer separation. The organic phase was then washed with brine (100 mL), dried over sodium sulfate and evaporated to dryness. The residue was recrystallized from hexane and dried in vacuum, yielding 5.85 g (85%) of compound 6 in the form of white crystals. $^1$HNMR ($CDCl_3$): δ=1.29 (s, 9H, C $(CH_3)_3$), 1.53 (s, 9H, Boc), 1.54 (s, 9H, Boc), 7.14 (d, 1H, 6-H), 7.17 (d, 1H, 5-H), 7.21 (s, 1H, 3-H). MS (DART, m/z): 367.21074 ($M+H^+$).

The 4-fluoro-diboc-catechol 1 standard compound was synthesized according to the above procedure with 4-fluoro-catechol as the starting material. $^1$HNMR ($CDCl_3$): δ=1.53 (d, 18H, Boc), 6.89-6.95 (m, 1H, 3-H), 7.02 (dd, 1H, 4-H), 7.19 (dd, 1H, 6-H). $^{19}$FNMR ($CDCl_3$): δ=−114.11. MS (DART, m/z): 329.13905 ($M+H^+$).

Compound 5 was synthesized according to the above procedure starting from 4-fluoro-catechol. 1HNMR ($CDCl_3$): δ=1.53 (d, 18H, Boc), 6.89-6.95 (m, 1H, 3-H), 7.02 (dd, 1H, 4-H), 7.19 (dd, 1H, 6-H). $^{19}$FNMR ($CDCl_3$): δ=−114.11. MS (DART, m/z): 329.13905 ($M+H^+$).

Compound 10 (3-fluoro-diboc-catechol) was synthesized according to the above procedure starting from 3-fluoro-catechol. $^1$HNMR ($CDCl_3$):1.56 (s, 18H, Boc), 6.92-7.00 (ddd, 1H, 5-H), 7.04-7.09 (dd, 1H, 6-H), 7.20-7.26 (dd, 1H, 3-H). $^{19}$FNMR ($CDCl_3$): δ=−126.65. MS (DART, m/z): 329.13888 ($M+H^+$).

EXAMPLE 3

Electrochemical Experiments

Electrochemical radiofluorination was conducted in a three-electrode system under a constant-potential mode controlled by an Autolab128 potentiostat-galvanostat (Metrohm USA). All electrochemical experiments were conducted in a cylindroid glass beaker cell with a total volume of 20 mL. During the experiments 6 mL of electrolyte was loaded. Two Pt mesh electrodes were used as the working (5.23 $cm^2$) and the counter (6.65 $cm^2$) electrodes. A leakless Ag/AgCl electrode (EDAQ Inc, USA) was used as the reference electrode.

The undivided cell was combined with a [$^{18}$F]fluoride ion delivery line. [$^{18}$F]fluoride was originally generated in 0.5 mL of [$^{18}$O]water from the cyclotron. The radioactivity was trapped on a MP-1® anion exchange resin by passing the above solution through. Majority of the water on the resin was removed by washing with 10 mL of anhydrous MeCN and drying with ultrapure Ar for 5 min. Then [$^{18}$F]fluoride was eluted out from the column with $Et_3N$. 3HF in different concentrations.

A pulsing technique, switching the potential from a high level to a low level periodically, was used to minimize the surface polymerization and poisoning issues. In this work, all electrolysis products were analyzed after 38 cycles of pulsing between 2.7 V (90 s) and 0.4 V (5 s).

EXAMPLE 4

Characterization Methods

Analytical HPLC for product identification was conducted using a Knauer K-501 HPLC pump, coupled with a Knauer K-2500 UV detector (254 nm) and a NaI (Tl) scintillation detector. A Gemini® HPLC column (150*4.6 mm, 5 μ) C18 column was used and eluted with MeOH/$H_2O$ (70/30; v/v) at a flow rate of 2.1 mL·$min^{-1}$. To analyze the regioselectivity of the reaction, MeOH/$H_2O$ (60/40; v/v) at a flow rate of 2.0 mL·$min^{-1}$ was used for clear separation of 4-fluoro-diboc-catechol 5 and 3-fluoro-diboc-catechol 10.

Alternatively, analytical HPLC for product identification was conducted using a Knauer K-501 HPLC pump, coupled with a Knauer K-2500 UV detector (254 nm) and a NaI (Tl) scintillation detector. A Luna® HPLC column (150*4.6 mm) C18 column was used and eluted with MeOH/$H_2O$ (70/30; v/v) at a flow rate of 2.1 mL·$min^{-1}$. From HPLC experiments, it has been found that some portion of radio activity could be trapped in the C18 column and the fluidic path. In order to make accurate calculation for the radio-fluorination efficiency, TLC measurements were performed on an AR-2000 TLC Imaging Scanner (Bioscan, Washington D.C., USA) radio-TLC instrument using dichlormethane as the single mobile phase.

In order to make accurate calculation for the radiofluorination efficiency, TLC measurements were performed on an AR-2000 TLC Imaging Scanner (Bioscan, Washington D.C., USA) using dichlormethane as the single mobile phase.

To purify the products of the reaction, water (30 mL) was added to the electrolyte solution and the mixture was passed through a Sep-Pak® C18 Classic Cartridge. Subsequently the product was eluted by 3 mL of methanol.

EXAMPLE 5

Cyclic Voltammetry

Figure 3:
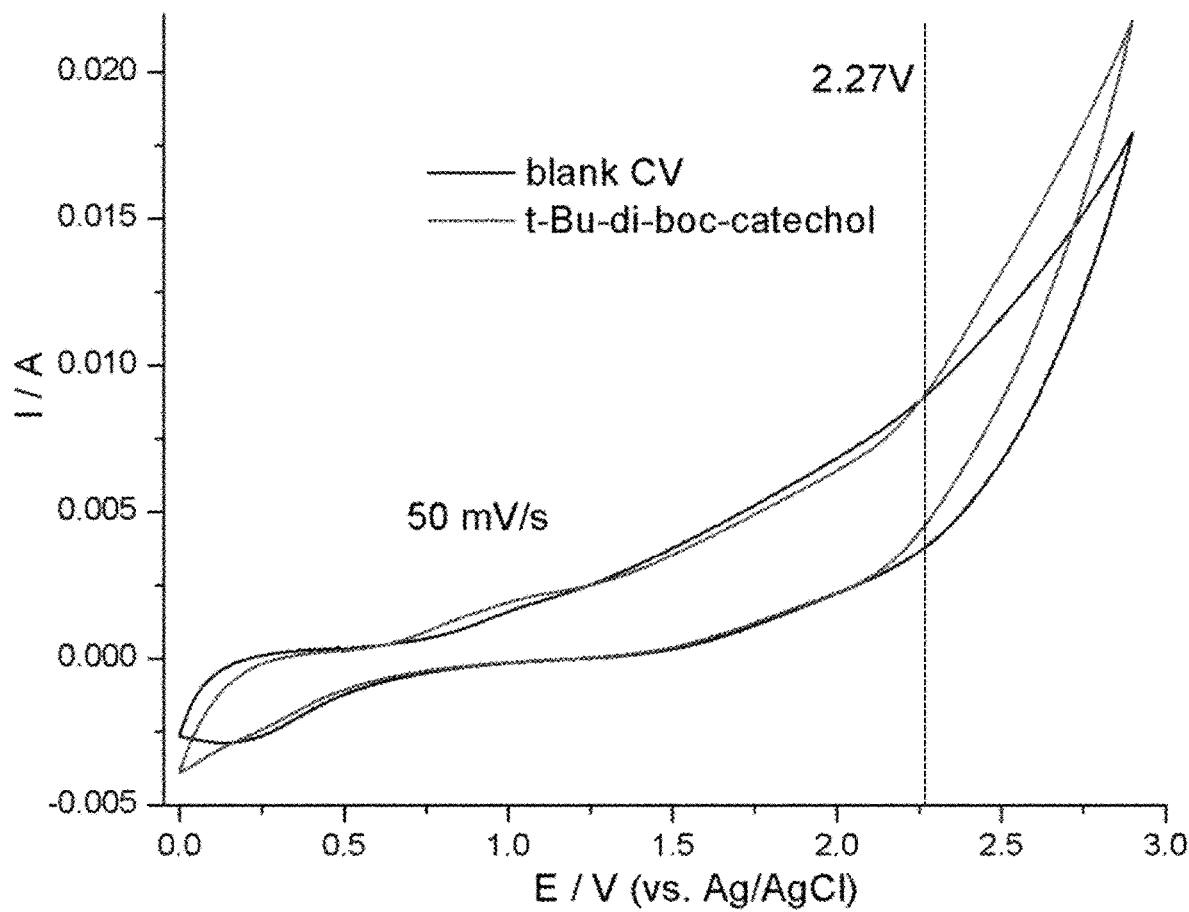
FIG. 3 shows the cyclic voltammogram of acetonitrile solution of $Et_3N \cdot 3HF$ (0.05 M) in the absence and presence of precursor 6 (see Example 5).

FIG. 3 shows the cyclic voltammogram of acetonitrile solution of $Et_3N$. 3HF (0.05 M) in the absence and presence of precursor 6. It can be seen that the $Et_3N$. 3HF electrolyte itself can be oxidized on the Pt working electrode with notable current beyond 0.85 V (vs. Ag/AgCl). However, upon addition of 0.005 M precursor 6, significant increase of current can be observed with the threshold (onset) of 2.27 V, indicating anodic oxidation and further fluorination of 6. While an oxidation potential higher than the onset at 2.27 V is required, increasing the potential will increase side products including any decomposition from the oxidation of 5 ($E_{onset}$=2.35 V). The best chemical yield (molar ratio of the fluorinated product and the precursor) was obtained at 2.7 V. As a result, for the experiments described herein, all electrolyses was performed under a potentiostatic condition of 2.7 V.

EXAMPLE 6

HPLC and TLC Results

HPLC traces with UV detection results and Gamma detection results of 6 using $Et_3N \cdot 3HF$ as the electrolyte were obtained by analyzing an aliquot (20 µl) of the raw sample. Peaks for the major product 5, the precursor 6 and side products were well separated and readily identified. Radio-fluorination efficiency was calculated based on the radio-TLC results. A typical radio-TLC trace for the electrolysis products with 0.05 M 6 and 0.05 M $Et_3N \cdot 3HF$. A single peak with Rf of 0.79 was attributed to 5, which matches the moving distance of the $^{19}F$ co-injected standard sample. All other non-reactive [$^{18}F$] or other [$^{18}F$] labeled products are ascribed to the main peak at the origin.

EXAMPLE 7

Radiofluorination Efficiency

Consumption rate of the precursor 6, chemical yield of 5 (based on the starting concentration of the precursor) and the radio-fluorination efficiency results are summarized in Table 1.

TABLE 1

[$^{18}F$]fluoride releasing efficiency using $Et_3N \cdot 3HAc$ in MeCN and radiofluorination efficiency with the precursor of 4-tert-butyl-diboc-catechol 2

| Concentration of $Et_3N \cdot 3HAc$/mM | Percentage of [$^{18}F$]fluoride released from the MP-1 ® cartridge/% | Radio-fluorination efficiency/% (n = 3) |
|---|---|---|
| 5 | 48 ± 4 | 2.1 ± 0.5 |
| 10 | 69 ± 5 | 3.4 ± 0.8 |
| 15 | 75 ± 8 | 0 |

*All radiofluorination experiments were performed at room temperature.

The consumption rate of the precursor remained rather stable as the concentration of the precursor changed. However, the chemical yield drops linearly as a function of the concentration of the precursor. Considering the formation of a cation radical as the prerequisite of anodic fluorination (Reischl et al., 2002, J. Radioanal. Nucl. Chem. 254, 409-411), a plausible explanation is the formation of dimers and/or polymers with increasing ratio of precursor to fluoride.(Belding et al., 2008, Journal of Physical Chemistry C 112, 1650-1657) Using only $Et_3N \cdot 3HF$ as the electrolyte at room temperature, a fluorination efficiency of 2.7±0.6% was achieved. To improve the solution conductivity, supporting electrolytes ($NBu_4ClO_4$ and $NBu_4PF_6$) were added and electrolysis was conducted as before. TLC results of electrochemical fluorination of 0.05 M 6 with 0.033 M $Et_3N$. $3HF$ in the absence and presence of 0.05 M $NBu_4ClO_4$, show that $NBu_4ClO_4$ increased radio-fluorination efficiency by a factor of five. In comparing the HPLC trace with and without $NBu_4ClO_4$, it can be seen that the formation of side products has been significantly hindered due to the presence of the supporting electrolyte.

The instability of the Boc protecting groups in acidic media similar to that used during electrolysis here is documented.(Namavari et al., 1992, Applied Radiation and Isotopes 43, 989-996). The unprotected t-Bu-catechol may be oxidized on Pt surface and passivate the electrode surface, which has a detrimental effect on radio-fluorination efficiency. The use of other protecting groups, adjusting the pH of the reaction mixture, lowering the reaction temperature, and the like, may alleviate this problem. To test this hypothesis, radiofluorination was conducted at 0° C. and the results were compared with those obtained at room temperature. The radiofluorination efficiency was observed to nearly double by lowering the T from 25° C. to 0° C. These results are consistent with those reported in the literature (see, for example, Kienzle et al., 2005, J. Labelled Compd. Radiopharm. 48, 259-273) Additionally, the effect of the supporting electrolyte was investigated by adding $NBu_4PF_6$ instead of $NBu_4ClO_4$. Similar to $NBu_4ClO_4$, $NBu_4PF_6$ was chosen due to its wide potential window (high stability) during electrolysis. The change resulting from the supporting electrolyte effect was minor and the best radiofluorination efficiency values were obtained using $NBu_4PF_6$ as the supporting electrolyte.

Although the yields (as measured by TLC) are instructive, actual recovered product yields (true radiochemical yields) may be of more general interest from a practical point of view. The product of 4-[$^{18}F$]fluoro-diboc-catechol was purified using Sep-Pak® C18 classic cartridges. Radiochemical purity was achieved (free [$^{18}F$]fluoride ions and [$^{18}F$] labelled side products were observed to have been removed efficiently). The decay corrected radiochemical yields were 8.9±1.6% (n=3) after 65 minutes with a synthesis time of 60 min and typical purification taking 5 min. These values indicate minimal loss of product during purification or co-elution of side products during TLC measurement. Furthermore, specific activity of the reaction, calculated from activity measurement of the radioactively pure product 4-fluoro-diboc-catechol gave a maximum specific activity value of 43 GBq/mmol, which is comparable to those reached by electrophilic fluorination with [18F]$F_2$.(Namavari et al., 1992; Reischl et al., 2002)

Finally, to exclude the possibility of formation of 3-[$^{18}F$] fluoro-diboc-catechol 10 HPLC was conducted with both standard isomers (5 and 10) as well as the products after purification.Only 4-[$^{18}F$]fluoro-diboc-catechol, with a retention time 1.3 min later than that of 10, was formed after electrochemical fluorination of 6. These results confirm the DFT results that the tert-butyl leaving group effectively directs the position of fluorination.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "a" and "an" and "the" and similar referents in the context of describing the invention (especially in the context of the following claims) are to be construed to cover both the singular and the plural, unless otherwise indicated herein or clearly contradicted by context. The terms "comprising", "having," "including," containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Applicants reserve the right to physically incorporate into this application any and all materials and information from any such articles, patents, patent applications, or other physical and electronic documents.

Other embodiments are set forth within the following claims.

What is claimed is:

1. A method of forming an [$^{18}$F] aryl fluoride compound, the method comprising a step of:

contacting an [$^{18}$F] fluoride source with an aryl compound comprising a reactive aryl carbon covalently bound to an electron donating leaving group within an electrochemical mixture comprising a solvent and an electrolyte; and allowing said [$^{18}$F] fluoride source to react with said reactive aryl ring carbon in the presence of an applied electrical current thereby forming said [$^{18}$F]aryl fluoride compound; wherein said [$^{18}$F]aryl fluoride compound is of formula (I):

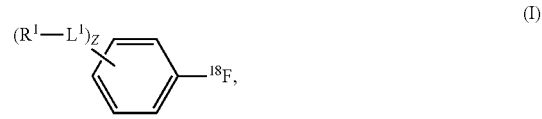

wherein, z is an integer from 0 to 10;

$L^1$ is independently —O—, —NH—, —S—, —C(O)NH—, —NHC(O)—, —NHNH—, —S(O)—, —S(O)$_2$—, —ONH—, or —NHO—;

$R^1$ is independently hydrogen, halogen, —N$_3$, —CF$_3$, —CCl$_3$, —CBr$_3$, —CI$_3$, —CN, —C(O)R$^{3A}$, —OR$^{3A}$, —NR$^{3A}$R$^{3B}$, —C(O)OR$^3$, —CONR$^{3A}$R$^{3B}$, —NR$^{3A}$R$^{3B}$C(O)R$^{3C}$, —NO$_2$, —SR$^{3A}$, —SO$_2$, —SO$_2$Cl, —SO$_3$R$^{3A}$, —SO$_2$NR$^{3A}$R$^{3B}$, —NHNR$^{3A}$R$^{3B}$, —ONR$^{3A}$R$^{3B}$, —NHC(O)NHR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{3A}$, $R^{3B}$ and $R^{3C}$ are independently hydrogen, halogen, —N$_3$, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and two $R^1$ subsitutents are optionally joined to from a substituted or unsubstituted cycloalkyl, substituted or unsubstituted heterocycloalkyl, substituted or unsubstituted aryl, or substituted or unsubstituted heteroaryl;

wherein said [$^{18}$F] aryl fluoride compound has a specific activity of more than 15 GBq/μmol; and wherein the electrolyte is tetrabutylammonium perchlorate (NBu$_4$ClO$_4$) or tetrabutylammonium hexafluorophosphate (NBu$_4$PF$_6$).

2. The method of claim 1, wherein said electrochemical mixture is a carrier free electrochemical mixture.

3. The method of claim 1, wherein said electrochemical mixture is a carrier added electrochemical mixture.

4. A method of forming an [$^{18}$F] aryl fluoride compound, the method comprising a step of:

contacting a [$^{18}$F] fluoride source with an aryl compound comprising a reactive aryl carbon covalently bound to an electron donating leaving group within an electrochemical mixture, wherein the mixture comprises a solvent and an electrolyte; and allowing said [$^{18}$F] fluoride source to react with said aryl compound in the presence of an applied electrical current;

wherein said aryl compound is of formula (II):

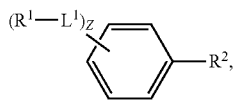

(II)

wherein:

z is an integer from 0 to 10;

L$^1$ is independently —O—, —NH—, —S—, —C(O)NH—, —NHC(O)—, —NHNH—, —S(O)—, —S(O)$_2$—, —ONH—, or —NHO—;

R$^1$ is independently hydrogen, halogen, —N$_3$, —CF$_3$, —CCl$_3$, —CBr$_3$, —CI$_3$, —CN, —C(O)R$^{3A}$, —OR$^{3A}$, —NR$^{3A}$R$^{3B}$, —C(O)OR$^3$, —CONR$^{3A}$R$^{3B}$, —NR$^{3A}$R$^{3B}$C(O)R$^{3C}$, —NO$_2$, —SR$^{3A}$, —SO$_2$, —SO$_2$Cl, —SO$_3$R$^{3A}$, —SO$_2$NR$^{3A}$R$^{3B}$,—NHNR$^{3A}$R$^{3B}$,—ONR$^{3A}$R$^{3B}$,—NHC(O)NHR$^{3A}$R$^{3B}$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^2$ is an electron donating leaving group;

R$^{3A}$, R$^{3B}$ and R$^{3C}$ are independently hydrogen, halogen, —N$_3$, —CF$_3$, —CCl$_3$, —CBr$_3$, —CI$_3$, —CN, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and two R$^1$ subsitutents are optionally joined to from a substituted or unsubstituted cycloalkyl, substituted or unsubstituted heterocycloalkyl, substituted or unsubstituted aryl, or substituted or unsubstituted heteroaryl;

with the proviso that the electrochemical mixture is a carrier free reaction media substantially lacking added $^{19}$F species; and wherein the electrolyte is tetrabutylammonium perchlorate (NBu$_4$ClO$_4$) or tetrabutylammonium hexafluorophosphate (NBu$_4$PF$_6$).

5. The method of claim 1, wherein the [$^{18}$F] aryl fluoride compound has a specific activity of more than 20 GBq/µmol.

6. The method of claim 5, wherein the [$^{18}$F] aryl fluoride compound has a specific activity of more than 43 GBq/µmol.

7. The method of claim 6, wherein the $^{18}$F] aryl fluoride compound has a specific activity of more than 50 GBq/µmol.

8. The method of claim 4, wherein the carrier free electrochemical mixture comprises triethylammonium acetate.

9. The method of claim 3, wherein the added carrier electrochemical mixture comprises a molecule or an ion capable of interacting with other molecules in such a manner as to transfer an $^{19}$F or $^{18}$F atom upon absorbing same on a solid support.

10. The method of claim 4, wherein the electrochemical mixture is anhydrous.

11. The method of claim 10, wherein said electrochemical mixture comprises acetonitrile as a solvent.

* * * * *